United States Patent [19]
Steiner et al.

[11] Patent Number: 5,945,441
[45] Date of Patent: Aug. 31, 1999

[54] PYRROLIDINE CARBOXYLATE HAIR REVITALIZING AGENTS

[75] Inventors: Joseph P. Steiner, Hampstead; Gregory S. Hamilton, Catonsville, both of Md.

[73] Assignee: Gpi Nil Holdings, Inc., Wilmington, Del.

[21] Appl. No.: 08/869,426

[22] Filed: Jun. 4, 1997

[51] Int. Cl.[6] .................. A61K 31/40; A61K 31/435
[52] U.S. Cl. .................. 514/427; 514/277; 514/336; 514/342; 514/343; 514/880
[58] Field of Search .................. 514/277, 336, 514/343, 880, 427, 342

[56] References Cited

U.S. PATENT DOCUMENTS

| | | |
|---|---|---|
| 4,996,193 | 2/1991 | Hewitt et al. . |
| 5,189,042 | 2/1993 | Goulet et al. . |
| 5,192,773 | 3/1993 | Armistead et al. . |
| 5,208,241 | 5/1993 | Ok et al. . |
| 5,258,389 | 11/1993 | Goulet et al. . |
| 5,284,826 | 2/1994 | Eberle . |
| 5,284,840 | 2/1994 | Rupprecht et al. . |
| 5,284,877 | 2/1994 | Organ et al. . |
| 5,292,747 | 3/1994 | Davis et al. . |
| 5,342,625 | 8/1994 | Hauer et al. . |
| 5,385,918 | 1/1995 | Connell et al. . |
| 5,457,111 | 10/1995 | Luly et al. . |
| 5,470,878 | 11/1995 | Michnick et al. . |
| 5,506,228 | 4/1996 | Norton et al. . |
| 5,532,248 | 7/1996 | Goulet et al . |
| 5,614,547 | 3/1997 | Hamilton et al. . |

FOREIGN PATENT DOCUMENTS

| | | |
|---|---|---|
| 0 423 714 A2 | 4/1991 | European Pat. Off. . |
| 0 564 924 A2 | 10/1993 | European Pat. Off. . |
| WO 96/41609 | 12/1996 | WIPO . |
| WO 97/36869 | 10/1997 | WIPO . |

OTHER PUBLICATIONS

Birkenshaw, T.N. et al., "Synthetic FKBP12 Ligands. Design and Synthesis of Pyranose Replacements," *Bioorganic & Medicinal Chemistry Letters*, (1994) 4:21, 2501–2506.

Caffrey, M.V. et al., "Synthesis and Evaluation of Dual Domain Macrocyclic FKBP12 Ligands," *Bioorganic & Medicinal Chemistry Letters*, (1994) 4:21, 2507–2510.

Hauske, J.R. et al. "Design and Synthesis of Novel FKBP Inhibitors," *J. of Medicinal Chemistry*, (1992) 35, 4284–4296.

Holt, D.A. et al., "Design, Synthesis, and Kinetic Evaluation of High–Affinity FKBP Ligands and the X–ray Crystal Structures of Their Complexes with FKBP12," *J. Am. Chem. Soc.*, (1993) 115, 9925–9938.

Holt, D.A. et al., "Structure–Activity Studies of Synthetic FKBP Ligands as Peptidyl–prolyl Isomers Inhibitors," *Bioorganic & Medicinal Chemistry Letters*, (1994) 4:2, 315–320.

Holt, D.A. et al., "Structure–Activity Studies of Nonmacrocyclic Rapamycin Derivatives," *Bioorganic & Medicinal Chemistry Letter*, (1993) 3:10, 1977–1980.

Luengo, J.I. et al., "Synthesis and Structure–Activity Relationships of Macrocyclic FKBP Ligands," *Bioorganic & Medicinal Chemistry Letters*, (1994) 4:2, 321–324.

Snyder, S.H. et al., "Immunophilins and the Nervous System," *Nature Medicine*, (1995) 1:1, 32–37.

Teague, S.J. et al., "Synthesis and Study of a Non–Macrocyclic FK506 Derivative," *Bioorganic & Medicinal Chemistry Letters*, (1994) 4:13, 1581–1584.

Teague, S.J. et al., "The Affinity of the Excised Binding Domain of FK–506 for the Immunophilin FKBP12," *Bioorganic & Medicinal Chemistry Letters*, (1993) 3:10, 1947–1950.

Wang, G.T. et al., "Synthesis and FKBP Binding of Small Molecule Mimics of the Tricarbonyl Region of FK506," *Bioorganic and Medicinal Chemistry Letters*, (1994) 4:9, 1161–1166.

Yamashita, D.S. et al., "Design, Synthesis and Evaluation of Dual Domain FKBP Ligands," *Bioorganic & Medicinal Chemistry*, (1994) 4:2, 325–328.

Iwabuchi, T. et al., "Effects of immunosuppressive peptidyl–prolyl cis–trans isomerase (PPIase inhibitors, cyclosporin A, FK506, ascomycin and rapamycin, on hair growth initiation in mouse: immunosuppression is not required for hair growth," *J. of Deramatol. Sci.*, (1995) 9:1, 64–69.

Yamamoto, S. et al., "Stimulation of hair growth by topical application of FK506, a potent immunosuppressive agent," *J. Invest. Dermatol*, (1994) 102:2, 160–164.

Jiang, H. et al., "Induction of anagen in telogen mouse skin by topical application of FK506, a potent immunosuppressant," *J. Invest. Dermatol.*, (1995) 104:4, 523–525.

CA126:272710, Steiner et al, 1997.

*Primary Examiner*—Rebecca Cook
*Attorney, Agent, or Firm*—Nath & Associates; Gary M. Nath; Todd L. Juneau

[57] ABSTRACT

This invention relates to methods of treating hair loss, through hair revitalization and germination, by administering non-immunosuppresive pyrrolidine carboxylate compounds.

15 Claims, 4 Drawing Sheets

PYRROLIDINE CARBOXYLATE HAIR REVITALIZING AGENTS

BACKGROUND OF THE INVENTION

1. Field of the Invention

This invention relates to methods of treating hair loss and stimulating the revitalization and germination of hair. More particularly, it relates to methods of administering pyrrolidine carboxylate compounds as novel agents for treatment of hair loss and for the germination and revitalization of hair.

2. Description of the Related Art

Hair loss occurs in a variety of situations. These situations include male pattern alopecia, alopecia senilis, alopecia areata, diseases accompanied by basic skin lesions or tumors, or systematic disorders such as nutritional disorders and internal secretion disorders. The mechanisms causing hair loss are very complicated but in some instances can be attributed to aging, genetic disposition, the activation of male hormones, the loss of blood supply to hair follicles, and scalp abnormalities.

The immunosuppressant drugs FK506, rapamycin and cyclosporin are well-known as potent T-cell specific immunosuppressants, and are effective against graft rejection after organ transplantation. It has been reported that topical, but not oral, application of FK506 (Yamamoto et al, J. Invest. Dermatol, 1994, 102, 160–164; Jiang et al., J. Invest. Dermatol. 1995, 104, 523–525) and cyclosporin (Iwabuchi et al, J. Dermatol. Sci. 1995, 9, 64–69) stimulated hair growth in a dose-dependent manner. One form of hair loss, alopecia areata, is known to be associated with autoimmune activities, hence, immunomodulatory compounds were expected to demonstrate efficacy for treating that type of hair loss. The hair growth stimulating effects of FK506 have been the subject of an international patent filing covering FK506 and structures related thereto for hair growth stimulation (Honbo et al., EP 0 423 714 A2). Honbo et al. discloses the use of relatively large tricyclic compounds, known for their immunosuppressive effects, as hair revitalizing agents.

The hair growth and revitalization effects of FK506 and related agents are disclosed in many U.S. patents. (Goulet et al., U.S. Pat. No. 5,258,389; Luly et al., U.S. Pat. No. 5,457,111; Goulet et al., U.S. Pat. No. 5,532,248; Goulet et al., U.S. Pat. No. 5,189,042; and Ok et al., U.S. Pat. No. 5,208,241; Rupprecht et al., U.S. Pat. No. 5,284,840; Organ et al., U.S. Pat. No. 5,284,877). These patents claim FK506 related compounds. Although they do not claim methods of hair revitalization, they disclose the known use of FK506 for effecting hair growth. Similar to FK506 (and the claimed variations in the Honbo et al. patent) the compounds claimed in these patents are relatively large. Further, the cited patents relate to immunomodulatory compounds for use in autoimmune related diseases, for which FK506's efficacy is well known.

Other U.S. Patents disclose the use of cyclosporin and related compounds for hair revitalization. (Hauer et al., U.S. Pat. No. 5,342,625; Eberle, U.S. Pat. No. 5,284,826; Hewitt et al., U.S. Pat. No. 4,996,193). These patents also relate to compounds useful for treating autoimmune diseases and cite the known use of cyclosporin and related immunosuppressive compounds for hair growth.

However, immunosuppressive compounds by definition suppress the immune system and also exhibit other toxic side effects. Accordingly, there is a need for non-immunosuppressant, small molecule compounds which are useful as hair revitalizing compounds.

Hamilton and Steiner disclose novel pyrrolidine carboxylate compounds which bind to the immunophilin FKBP12 and stimulate nerve growth but which lack immunosuppressive effects, in U.S. Pat. No. 5,614,547. Unexpectedly, it has been discovered that these non-immunosuppressant compounds promote hair growth with an efficacy similar to FK506. Yet their novel small molecule structure and non-immunosuppressive properties differentiate them from FK506 and related immunosuppressive compounds found in the prior art.

SUMMARY OF THE INVENTION

The present invention relates to methods of treating hair loss by administering pyrrolidine carboxylate compounds, and particularly N-glyoxyl prolyl esters, as novel hair revitalizing, germination, and regrowth compounds. Although these compounds are known as having an affinity for FKBP-type immunophilins, they are unexpectedly potent as hair growth agents. A key feature of the compounds of the present invention is that they do not exert any significant immunosuppressive activity in addition to their hair growth activity.

A preferred embodiment of this invention is a method of revitalizing hair growth which comprises: administering to an animal an effective amount of a non-immunosuppressive pyrrolidine carboxylate compound.

Another preferred embodiment of this invention is a method of hair germination which comprises: administering to an animal an effective amount of a non-immunosuppressive pyrrolidine carboxylate compound.

Another preferred embodiment of this invention is a method of preventing hair loss which comprises: administering to an animal an effective amount of a pyrrolidine carboxylate compound.

Another preferred embodiment of this invention is the treatment of male pattern alopecia, alopecia senilis, alopecia areata, hair loss from skin lesions or tumors, and hair loss from systematic disorders such as nutritional disorders and internal secretion disorders which comprises: administering to an animal an effective amount of a pyrrolidine carboxylate compound.

Another preferred embodiment of this invention is the treatment of hair loss resulting from chemotherapy which comprises: administering to an animal an effective amount of a pyrrolidine carboxylate compound.

Another preferred embodiment of this invention is the treatment of hair loss resulting from radiation which comprises: administering to an animal an effective amount of a pyrrolidine carboxylate compound.

Another preferred embodiment of this invention is the treatment of hair loss which comprises: administering to an animal an effective amount of a pyrrolidine carboxylate compound.

Yet another embodiment of this invention is treating hair loss and stimulating revitalization and germination which comprises: administering to an animal an effective amount of a N-(glyoxyl)prolyl ester.

BRIEF DESCRIPTION OF THE DRAWINGS

FIG. 1 shows the condition of the mice prior to the experiment.

FIG. 2 shows that less than 3% of the shaved area is covered with new hair growth when the vehicle (control) is administered.

FIG. 3 shows the remarkable effects of the compounds of the present invention wherein 90% of the shaved area is covered with new hair growth.

FIG. 4 shows the remarkable ability of the compounds of the present invention to achieve, essentially, complete hair regrowth in the shaved area.

DETAILED DESCRIPTION OF THE INVENTION

Figure 1:
FIG. 1 is a photograph of C57 Black 6 mice before being shaved for the experiment.

The methods of this invention relate to treating hair loss and stimulating hair revitalization and germination, through the administration of novel non-immunosuppressive hair growth agents. Preferred agents are generically described as pyrrolidine carboxylate compounds.

Preferred agents used in the present invention are compounds of Formula I:

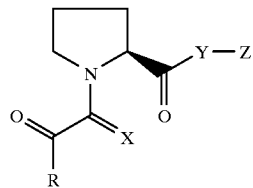

I wherein $R_1$ is selected from the group consisting of a $C_1-C_9$ straight or branched chain alkyl or alkenyl group optionally substituted with $C_3-C_8$ cycloalkyl, $C_3$ or $C_5$ cycloalkyl, $C_5-C_7$ cycloalkenyl, $Ar_1$, where said alkyl, alkenyl, cycloalkyl or cycloalkenyl groups may be optionally substituted with $C_1-C_4$ alkyl, $C_1-C_4$ alkenyl, or hydroxy, where $Ar_1$ is selected from the group consisting of 1-naphthyl, 2-naphthyl, 2-indolyl, 3-indolyl, 2-furyl, 3-furyl, 2-thiazolyl, 2-thienyl, 3-thienyl, 2-pyridyl,3-pyridyl,4-pyridyl, and phenyl, having one to three substituents which are independently selected from the group consisting of hydrogen, halo, hydroxyl, nitro, trifluoromethyl, $C_1-C_6$ straight or branched alkyl or alkenyl, $C_1-C_4$ alkoxy or $C_1-C_4$ alkenyloxy, phenoxy, benzyloxy, and amino:

X is selected from the group consisting of oxygen, sulfur, methylene ($CH_2$), or $H_2$;

Y is selected from the group consisting of oxygen or $NR_2$, where $R_2$ is hydrogen or $C^1-C_6$ alkyl; and Z is selected from the group consisting of $C_2-C_6$ straight or branched chain alkyl or alkenyl, wherein the alkyl chain is substituted in one or more positions with $Ar_1$ as defined above, $C_3-C_8$ cycloalkyl, cycloalkyl connected by a $C_1-C_6$ straight or unbranched alkyl or alkenyl chain, and $Ar_2$ is selected from the group consisting of 2-indolyl, 3-indolyl, 2-furyl, 3-furyl, 2-thiazolyl, 2-thienyl, 3-thienyl, 2-pyridyl, 3-pyridyl, 4-pyridyl, and phenyl, having one to three substituents which are independently selected from the group consisting of hydrogen, halo, hydroxyl, nitro, trifluoromethyl, $C_1-C_6$ straight or branched alkyl or alkenyl, $C_1-C_4$ alkoxy or $C_1-C_4$ alkenyloxy, phenoxy, benzyloxy, and amino; Z may also be the fragment:

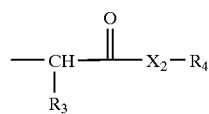

wherein $R_3$ is selected from the group consisting of straight or branched alkyl $C_1-C_8$ optionally substituted with $C_3-C_8$ cycloalkyl, or $Ar_1$ as defined above, and unsubstituted $Ar_1$;

$X_2$ is O or $NR_5$, where $R_5$ is selected from the group consisting of hydrogen, $C_1-C_6$ straight or branched alkyl and alkenyl;

$R_4$ is selected from the group consisting of phenyl, benzyl, $C_1-C_5$ straight or branched alkyl or alkenyl, and $C_1-C_5$ straight or branched alkyl or alkenyl substituted with phenyl; or pharmaceutically acceptable salts or hydrates thereof.

Other preferred agents used in the present invention are N-(glyoxyl)prolyl ester compounds of Formula II:

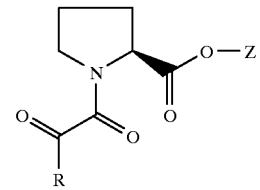

II wherein $R_1$ is a $C_1-C_9$ straight or branched chain alkyl or alkenyl group optionally substituted with $C_3-C_8$ cycloalkyl, $C_3$ or $C_5$ cycloalkyl, $C_5-C_7$ cycloalkenyl, or $Ar_1$, where said alkyl, alkenyl, cycloalkyl or cycloalkenyl groups may be optionally substituted with $C_1-C_4$ alkyl, $C_1-C_4$ alkenyl, or hydroxy, and where Ar1 is selected from the group consisting of 1-naphthyl, 2-naphthyl, 2-indolyl, 3-indolyl, 2-furyl, 3-furyl, 2-thiazolyl, 2-thienyl, 3-thienyl, 2-pyridyl, 3-pyridyl, or 4-pyridyl, or phenyl, having one to three substituents which are independently selected from the group consisting of hydrogen, halo, hydroxyl, nitro, trifluoromethyl, $C_1-C_6$ straight or branched alkyl or alkenyl, $C_1-C_4$ alkoxy or $C_1-C_4$ alkenyloxy, phenoxy, benzyloxy, and amino;

Z is a $C_2-C_6$ straight or branched chain alkyl or alkenyl, wherein the alkyl chain is substituted in one or more positions with $Ar_1$ as defined above, $C_3-C_8$ cycloalkyl, cycloalkyl connected by a $C_1-C_6$ straight or unbranched alkyl or alkenyl chain, or $Ar_2$ where $Ar_2$ is selected from the group consisting ot 2-indolyl, 3-indolyl, 2-furyl, 3-furyl, 2-thiazolyl, 2-thienyl, 3-thienyl, 2-pyridyl, 3-pyridyl, 4-pyridyl, or phenyl, having one to three substituents which are independently selected from the group consisting of hydrogen, halo, hydroxyl, nitro trifluoromethyl, $C_1-C_6$ straight or branched alkyl or alkenyl, $C_1-C_4$ alkoxy or $C_1-C_4$ alkenyloxy, phenoxy, benzyloxy, and amino; or pharmaceutically acceptable salts or hydrates thereof.

Other preferred compounds of the invention include:
3-phenyl-1-propyl (2S)-1-(3,3-dimethyl-1,2-dioxopentyl)-2-pyrrolidinecarboxylate,
3-phenyl-1-prop-2-(E)-enyl (2S)-1-(3,3-dimethyl-1,2-dioxopentyl)-2-pyrrolidinecarboxylate, 3-(3,4,5-trimethoxyphenyl)-1-propyl (2S)-1-(3,3-dimethyl-1,2-dioxopentyl)-2-pyrrolidinecarboxylate,
3-(3,4,5-trimethoxyphenyl)-1-prop-2-(E)-enyl (2S)-1-(3,3dimethyl-1,2-dioxopentyl)-2-pyrrolidinecarboxylate,
3-(4,5-methylenedioxyphenyl)-1-propyl(2S) -1-(3,3dimethyl-1,2dioxopentyl)-2-pyrrolidinecarboxylate,
3-(4,5-methylenedioxyphenyl)-1-prop-2-(E)-enyl (2S)-1-(3,3dimethyl-1,2-dioxopentyl)-2-pyrrolidinecarboxylate,
3-cyclohexyl-1-propyl (2S)-1-(3,3-dimethyl-1,2-dioxopentyl)-2-pyrrolidinecarboxylate,
3-cyclohexyl-1-prop-2-(E)-enyl (2S)-1-(3,3-dimethyl-1,2dioxopentyl)-2-pyrrolidinecarboxylate,
(1R)-1,3-diphenyl-1-propyl (2S)-1-(3,3-dimethyl-1,2dioxopentyl)-2-pyrrolidinecarboxylate,
3-phenyl-1-propyl (2S)-1-(1,2-dioxo-2-[2-furanyl])ethyl-2-pyrrolidinecarboxylate,
3-phenyl-1-propyl (2S)-1-(1,2-dioxo-2-[2-thienyl])entyl-2-pyrrolidinecarboxylate,
3-phenyl-1-propyl (2S)-1-(1,2-dioxo-2-[2-thiazolyl])ethyl-2-pyrrolidinecarboxylate,
3-phenyl-1-propyl (2S)-1-(1,2-dioxo-2,phenyl)ethyl-2-pyrrolidinecarboxylate,
3-(2,5-dimethoxyphenyl)-1-propyl (2S)-1-(3,3-dimethyl-1,2-dioxopentyl)-2-pyrrolidinecarboxylate,
3-(2,5-dimethoxyphenyl)-1-prop-2-(E)-enyl(2S)-1-(3,3-dimethyl-1,2-dioxopentyl)-2-pyrrolidinecarboxylate,
2-(3,4,5-trimethoxyphenyl)-1-ethyl (2S)-1-(3,3-dimethyl-1,2-dioxopentyl)-2-pyrrolidinecarboxylate,
3-(3-Pyridyl)-1-propyl(2S)-1-(3,3-dimethyl-1,2-dioxopentyl)-2-pyrrolidinecarboxylate,
3-(2-Pyridyl)-1-propyl(2S)-1-(3,3-dimethyl-1,2-dioxopentyl)-2-pyrrolidinecarboxylate,
3-(4-Pyridyl)-1-propyl(2S)-1-(3,3-dimethyl-1,2-dioxopentyl)-2-pyrrolidinecarboxylate,
3-phenyl-1-propyl (2S)-1-(2-cyclohexyl-1,2-dioxoethyl)-2-pyrrolidinecarboxylate,
3-phenyl-1-propyl (2S)-1-(2-tert-butyl-1,2-dioxoethyl)-2-pyrrolidinecarboxylate,
3-phenyl-1-propyl (2S)-1-(2-cyclohexylethyl-1,2-dioxoethyl)-2-pyrrolidinecarboxylate,
3-(3-Pyridyl)-1-propyl (2S)-1-(2-cyclohexylethyl-1,2-dioxoethyl)-2-pyrrolidinecarboxylate,
3-(3-Pyridyl)-1-propyl (2S)-1-(2-tert-butyl-1,2-dioxoethyl)-2-pyrrolidinecarboxylate,
3,3-diphenyl-1-propyl (2S)-1-(3,3-dimethyl-1,2-dioxopentyl)-2-pyrrolidinecarboxylate,
3-(3-Pyridyl)-1-propyl (2S)-1-(2-cyclohexyl-1,2-dioxoethyl)-2-pyrrolidinecarboxylate,
3-(3-Pyridyl)-1-propyl (2S)-N-([2-thienyl]glyoxyl)pyrrolidinecarboxylate,
3,3-Diphenyl-1-propyl (2S)-1-(3,3-dimethyl-1,2-dioxobutyl)-2-pyrrolidinecarboxylate,
3,3-Diphenyl-1-propyl (2S)-1-cyclohexylglyoxyl-2-pyrrolidinecarboxylate,
3,3-Diphenyl-1-propyl (2S)-1-(2-thienyl)glyoxyl-2-pyrrolidinecarboxylate, and a pharmaceutically acceptable salt, hydrate, or a mixture thereof.

The term "N-(glyoxyl)prolyl ester" refers to compounds of Formula II.

The term "pyrrolidine carboxylate" refers to compounds of Formula I and includes N-(glyoxyl)prolyl esters within the definition.

The methods of the present invention use compounds which can be used in the form of salts derived from inorganic or organic acids and bases. Included among such acid salts are the following: acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemissulfate heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, propionate, succinate, tartrate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The hair revitalization compounds of this invention can be periodically administered to a patient suffering from a hair loss or improper hair growth condition. The compounds can also be administered to mammals other than humans for treatment of various conditions necessitating the prevention of hair loss, hair revitalization, or hair germination.

The novel hair revitalization agents of the present invention are potent inhibitors of rotamase activity and are non-immunosuppressive. Further, for the purposes of this invention, the use of those compounds is effective in hair revitalization and germination. This activity is useful to promote hair growth in treating alopecia, male pattern alopecia, alopecia senilis, alopecia areata, diseases accompanied by basic skin lesions or tumors, or systematic disorders such as nutritional disorders and internal secretion disorders.

To be effective therapeutically as treatments for conditions associated with hair loss the agents must readily effect the targeted areas. For these purposes the compounds of the present invention may be administered topically in dosage formulations containing conventional non-toxic pharmaceutically acceptable carriers.

For application topically to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

The compounds can be administered with other hair revitalizing agents. The dosage level of other hair growth drugs will depend upon the factors previously stated and the effectiveness of the drug combination.

SYNTHESIS OF THE COMPOUNDS

Compounds of the invention may be readily prepared as described in Scheme I, below.

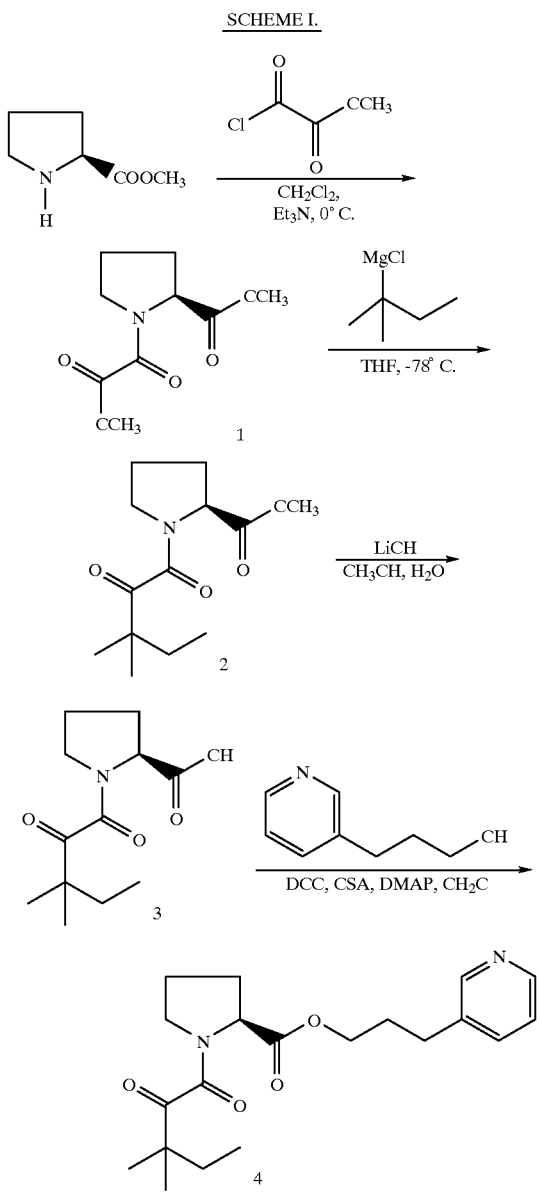

EXAMPLES

The following examples are illustrative of preferred embodiments of methods of use and preparation of compounds of the invention and are not to be construed as limiting the invention thereto. Unless otherwise indicated, all percentages are based upon 100% of the final formulations.

Example 1

Synthesis of 3-(3-Pyridyl)-1-propyl (2S)-1-(3,3-dimethyl-1,2-dioxopentyl)-2-pyrrolidinecarboxylate. ("GPI 1046")

Synthesis of methyl (2S)-1-(1,2-dioxo-2-methoxyethyl)-2-pyrrolidinecarboxylate (1).

A solution of L-proline methyl ester hydrochloride (3.08 g; 18.60 mmol) in dry methylene chloride was cooled to 0° C. and treated with triethylamine (3.92 g; 38.74 mmol; 2.1 eq). After stirring the formed slurry under a nitrogen atmosphere for 15 minutes, a solution of methyl oxalyl chloride (3.20 g; 26.12 mmol) in methylene chloride (45 mL) was added dropwise. The resulting mixture was stirred at 0° C. for 1.5 hour. After filtering to remove solids, the organic phase was washed with water, dried over MgSO$_4$ and concentrated. The crude residue was purified on a silica gel column, eluting with 50% ethyl acetate in hexane, to obtain 3.52 g (88%) of the product as a reddish oil. Mixture of cis-trans amide rotamers; data for trans rotamer given. $^1$H NMR (CDCl$_3$): δ 1.93 (dm, 2H); 2.17 (m, 2H); 3.62 (m, 2H); 3.71 (s, 3H); 3.79, 3.84 (s, 3H total); 4.86 (dd, 1H, J=8.4, 3.3).

Synthesis of methyl (2S)-1-(1,2-dioxo-3,3-dimethylpentyl)-2-pyrrolidinecarboxylate (2).

A solution of methyl (2S)-1-(1,2-dioxo-2-methoxyethyl)-2-pyrrolidinecarboxylate (2.35 g; 10.90 mmol) in 30 mL of tetrahydrofuran (THF) was cooled to −78° C. and treated with 14.2 mL of a 1.0 M solution of 1,1-dimethylpropylmagnesium chloride in THF. After stirring the resulting homogeneous mixture at −78° C. for three hours, the mixture was poured into saturated ammonium chloride (100 mL) and extracted into ethyl acetate. The organic phase was washed with water, dried, and concentrated, and the crude material obtained upon removal of the solvent was purified on a silica gel column, eluting with 25% ethyl acetate in hexane, to obtain 2.10 g (75%) of the oxamate as a colorless oil. $^1$H NMR (CDCl$_3$) : δ 0.88 (t, 3H); 1.22, 1.26 (s, 3H each); 1.75 (dm, 2H); 1.87–2.10 (m, 3H); 2.23 (m, 1H); 3.54 (m, 2H); 3.76 (s, 3H); 4.52 (dm, 1H, J=8.4, 3.4).

Synthesis of (2S)-1-(1,2-dioxo-3,3-dimethylpentyl)-2-pyrrolidinecarboxylic acid (3).

A mixture of methyl (2S)-1-(1,2-dioxo-3,3-dimethylpentyl)-2-pyrrolidinecarboxylate (2.10 g; 8.23 mmol), 1N LiOH (15 mL), and methanol (50 mL) was stirred at 0° C. for 30 minutes and at room temperature overnight. The mixture was acidified to pH 1 with 1 N HCl, diluted with water, and extracted into 100 mL of methylene chloride. The organic extract was washed with brine and concentrated to deliver 1.73 g (87%) of snow-white solid which did not require further purification. $^1$H NMR (CDCl$_3$): δ 0.87 (t, 3H); 1.22, 1.25 (s, 3H each); 1.77 (dm, 2H); 2.02 (m, 2H); 2.25 (m, 1H); 3.53 (dd, 2H, J=10.4, 7.3); 4.55 (dd, 1H, J=8.6, 4.1).

Synthesis of 3-(3-pyridyl)-1-propyl(2S)-1-(3,3-dimethyl-1,2-dioxopentyl)-2-pyrrolidinecarboxylate (4).

A mixture of (2S)-1-(1,2-dioxo-3,3-dimethylpentyl)-2-pyrrolidinecarboxylic acid (4.58 g; 19 mmol), 3-pyridinepropanol (3.91 g; 28.5 mmol), dicyclohexylcarbodiimide (6.27 g; 30.4 mmol), camphorsulphonic acid (1.47 g; 6.33 mmol) and 4-dimethyl aminopyridine (773 mg; 6.33 mmol) in methylene chloride (100 mL) was stirred overnight under a nitrogen atmosphere. The reaction mixture was filtered through Celite to remove solids and concentrated in vacuo. The crude material was triturated with several portions of ether, and the ether portions were filtered through Celite to remove solids and concentrated in vacuo. The concentrated filtrate was purified on a flash column (gradient elution, 25% ethyl acetate in hexane to pure ethyl acetate) to obtain 5.47 g (80%) of GPI 1046 as a colorless oil (partial hydrate). $^1$H NMR (CDCl$_3$, 300 MHz): δ 0.85 (t, 3H); 1.23, 1.26 (s, 3H each); 1.63–1.89 (m, 2H); 1.90–2.30 (m, 4H); 2.30–2.50 (m, 1H); 2.72 (t, 2H); 3.53 (m, 2H); 4.19 (m, 2H); 4.53 (m, 1H); 7.22 (m, 1H); 7.53 (dd, 1H); 8.45 Anal. Calcd. for C$_{20}$H$_{28}$NO$_4$—0.25 H$_2$O: C, 65.82; H, 7.87; N, 7.68, Found: C, 66.01; H, 7.85; N, 7.64.

Example 2

Hair Revitalizing Test Example

In Vivo Hair Generation Test With C57 Black 6 Mice

Figure 2:
FIG. 2 is a photograph of mice treated with vehicle (Example 2) after six weeks.
Figure 3:
FIG. 3 is a photograph of mice treated with of 10 μM of GPI 1046 (Example 2) after six weeks.
Figure 4:
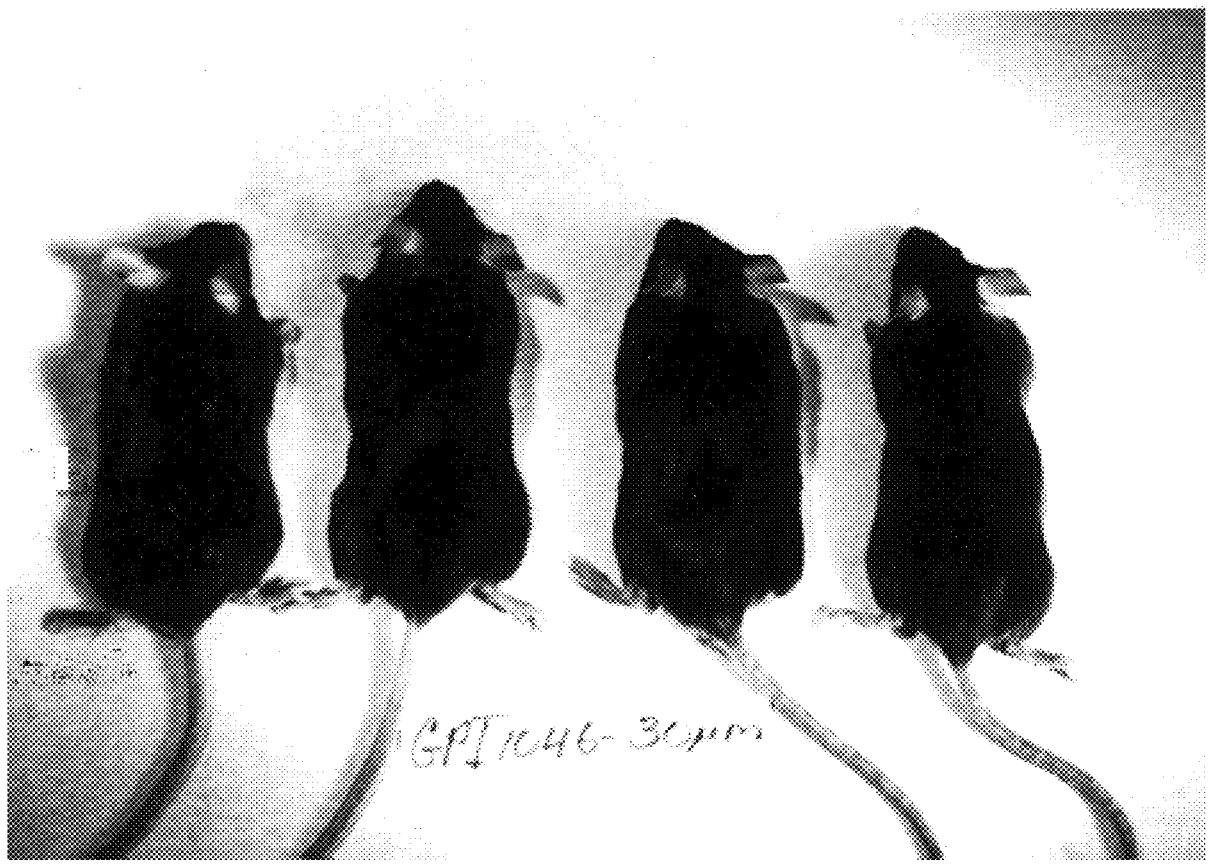
FIG. 4 is a photograph of mice treated with 30 μM of GPI 1046 (Example 1) after six weeks.

C57 black 6 mice were used to demonstrate the hair revitalizing properties of Example 1. Referring now to FIGS. 1 and 2 of the drawings, C57 black 6 mice, approximately 7 weeks old, had an area of about 2 inches by 2 inches on their hindquarters shaved to remove all existing hair. Care was taken not to nick or cause abrasion to the underlaying dermal layers. The animals were in anagen growth phase, as indicated by the pinkish color of the skin. Referring now to FIGS. 2, 3 and 4, four animals per group were treated by topical administration with 20% propylene glycol vehicle (FIG. 2), 10 μM Example 1 ("GPI 1046") (FIG. 3) or 30 μM Example 1 ("GPI 1046") (FIG. 4) dissolved in the vehicle. The animals were treated with vehicle or Example 1 ("GPI 1046") every 48 hours (3 applications total over the course of 5 days) and the hair growth was allowed to proceed for 6 weeks. Hair growth was quantitated by the percent of shaved area covered by new hair growth during this time period.

FIG. 2 shows that animals treated with vehicle only showed a small amount of hair growth in patches or tufts, with less than 3% of the shaved area covered with new growth. In contrast, FIG. 3 shows that animals treated with 10 μM Example 1 ("GPI 1046") showed dramatic hair growth, covering greater than 90% of the shaved area in all animals. Further, FIG. 4 shows that mice treated with 30 μM Example 1 ("GPI 1046") showed essentially complete hair regrowth and their shaved areas were indistinguishable from unshaven C57 black 6 mice.

Example 3

A lotion comprising the composition shown below may be prepared.

|  | (%) |
|---|---|
| 95% Ethanol | 80.0 |
| GPI 1046 | 10.0 |
| α-Tocopheral acetate | 0.01 |
| Ethylene oxide (40 mole) adducts of hardened castor oil | 0.5 |
| purified water | 9.0 |
| perfume and dye | q.s. |

Into 95% ethanol are added GPI 1046, α-tocopherol acetate, ethylene oxide (40 mole) adducts of hardened castor oil, perfume and a dye, and the mixture is stirred and dissolved, followed by an addition of purified water, to obtain a transparent liquid lotion.

The lotion is coated once or twice per day, in an amount of 5 ml each time, at a site having marked baldness or alopecia.

Example 4

A lotion comprising the composition shown below may be prepared.

|  | (%) |
|---|---|
| 95% Ethanol | 80.0 |
| GPI 1046 | 0.005 |
| Hinokitiol | 0.01 |
| Ethylene oxide (40 mole) adducts of hardened castor oil | 0.5 |
| Purified water | 19.0 |
| Perfume and dye | q.s. |

Into 95% ethanol are added GPI 1046, hinokitiol, ethylene oxide (40 mole) adducts of hardened castor oil, perfume, and a dye, and the mixture is stirred and dissolved, followed by an addition of purified water, to obtain a transparent liquid lotion.

The lotion is coated by spraying once to 4 times per day.

Example 5

An emulsion may be prepared from A phase and B phase having the following compositions.

|  | (%) |
|---|---|
| (A phase) |  |
| Wale wax | 0.5 |
| Cetanol | 2.0 |
| Petrolatum | 5.0 |
| Squalane | 10.0 |
| Polyoxyethylene (10 mole) momostearate | 2.0 |
| Sorbitane monooleate | 1.0 |
| GPI 1046 | 0.01 |
| (B phase) |  |
| Glycerine | 10.0 |
| Purified water | 69.0 |
| Perfume, dye, and preservative | q.s. |

The A phase and the B phase are respectively heated and melted and maintained at 80° C., both phases are mixed to be emulsified, and are cooled under stirring to normal temperature to obtain an emulsion.

The emulsion is coated by spraying once to four times per day.

Example 6

A cream may be prepared from A phase and B phase having the following compositions.

|  | (%) |
|---|---|
| (A Phase) |  |
| Fluid paraffin | 5.0 |
| Cetostearyl alcohol | 5.5 |
| Petrolatum | 5.5 |
| Glycerine monostearate | 33.0 |
| Polyoxyethylene (20 mole) 2-octyldodecyl ether | 3.0 |
| Propylparaben | 0.3 |
| (B Phase) |  |
| GPI 1046 | 0.8 |
| Glycerine | 7.0 |
| Dipropylene glycol | 20.0 |
| Polyethylene glycol 4000 | 5.0 |

-continued

|  | (%) |
| --- | --- |
| Sodium Hexametaphosphate | 0.005 |
| Purified water | 44.895 |

The A phase is heated and melted, and maintained at 70° C., the B phase is added into the A phase followed by stirring, and the obtained emulsion is cooled to obtain cream.

The cream is coated on the skin once to 4 times per day.

Example 7

A hair liquid comprising the composition shown below may be prepared.

|  | (%) |
| --- | --- |
| Polyoxyethylene butyl ether | 20.0 |
| Ethanol | 50.0 |
| GPI 1046 | 0.001 |
| Propylene glycol | 5.0 |
| Polyoxyethylene hardened castor oil derivative (ehtylene oxide 80 mole adducts) | 0.4 |
| Perfume | q.s. |
| Purified water | q.s. |

Into ethanol are added polyoxypropylene butyl ether, propylene glycol, polyoxyethylene hardened castor oil, GPI 1046, and perfume which are mixed under string, and to the mixture is added purified water, to obtain a hair liquid.

The liquid is coated on the skin once to 4 times per day.

Example 8

A hair shampoo comprising the composition shown below may be prepared.

|  | (%) |
| --- | --- |
| Sodium laurylsulfate | 5.0 |
| Triethanolamine laurylsulfate | 5.0 |
| Betaine layryldimethylaminoacetate | 6.0 |
| Ethylene glycol distearate | 2.0 |
| Polyethylene glycol | 5.0 |
| GPI 1046 | 5.0 |
| Ethanol | 2.0 |
| Perfume | 0.3 |
| Purified water | 69.7 |

Into 69.7 of purified water are added 5.0 g of sodium laurylsulfate, 5.0 g of triethanolamine laurylsulfate, 6.0 g of betaine lauryldimethylaminoacetate, then a mixture obtained by adding 5.0 g of GPI 1046, 5.0 g of polyethylene glycol, and 2.0 g of ethylene glycol distearate to 2.0 g of ethanol, followed by stirring, and 0.3 g of perfume, are successfully added, and the mixture is heated then cooled to obtain a hair shampoo.

The hair shampoo is used on the scalp once or twice per day.

Example 9

A patient is suffering from alopecia senilis. The compounds of the present invention would be administered to the patient. It would be expected that hair growth would occur.

Example 10

A patient is suffering from male alopecia. The compounds of the present invention would be administered to the patient. It would be expected that increased hair growth would occur.

Example 11

A patient is suffering from alopecia areata. The compounds of the present invention would be administered to the patient. It would be expected that increased hair growth would occur.

Example 12

A patient is suffering from hair loss resulting from skin lesions. The compounds of the present invention would be administered to the patient. It would be expected that increased hair growth would occur.

Example 13

A patient is suffering from hair loss resulting from tumors. The compounds of the present invention would be administered to the patient. It would be expected that increased hair growth would occur.

Example 14

A patient is suffering from hair loss resulting from a systematic disorder such as a nutritional disorder or internal secretion disorder. The compounds of the present invention would be administered to the patient. It would be expected that increased hair growth would occur.

Example 15

A patient is suffering from hair loss resulting from chemotherapy. The compounds of the present invention would be administered to the patient. It would be expected that increased hair growth would occur.

Example 16

A patient is suffering from hair loss resulting from radiation. The compounds of the present invention would be administered to the patient. It would be expected that increased hair growth would occur.

The invention being thus described, it will be obvious that the same may be varied in many ways. Such variations are not to be regarded as a departure from the spirit and scope of the invention and all such modifications are intended to be included within the scope of the following claims.

What is claimed is:

1. A method of promoting hair germination which comprises: administering to an animal an effective amount of a compound of the formula:

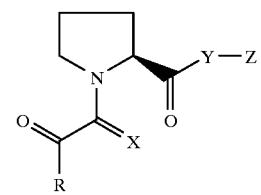

I wherein
R is selected from the group consisting of a $C_1$–$C_9$ straight or branched chain alkyl or alkenyl group optionally substituted with $C_3$–$C_8$ cycloalkyl, $C_5$–$C_7$ cycloalkenyl, and $Ar_1$, where said alkyl, alkenyl, cycloalkyl or cycloalkenyl groups are optionally substituted with $C_1$–$C_4$ alkyl, $C_1$–$C_4$ alkenyl, or hydroxy, where $Ar_1$ is selected from the group consisting of 1-naphthyl, 2-naphthyl, 2-indolyl, 3-indolyl, 2-furyl, 3-furyl, 2-thiazolyl, 2-thienyl, 3-thienyl, 2-,3-,4-pyridyl, and phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino;

X is selected from the group consisting of oxygen, sulphur, methylene, or $H_2$;

Y is selected from the group consisting of oxygen or $NR_2$, where $R_2$ is hydrogen or $C^1$–$C_6$ alkyl; and Z is selected from the group consisting of $C_2$–$C_6$ straight or branched chain alkyl or alkenyl, wherein the $C_2$–$C_6$ straight or branched chain alkyl is substituted in one or more positions with $Ar_1$ as defined above, $C_3$–$C_8$ cycloalkyl, or cycloalkyl connected by a $C_1$–$C_6$ straight alkyl or alkenyl chain; or Z is a fragment having the following formula:

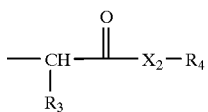

wherein $R_3$ is selected from the group consisting of $C_1$–$C_8$ straight or branched alkyl optionally substituted with $C_3$–$C_8$ cycloalkyl, $Ar_1$ as defined above, and unsubstituted $Ar_1$;

$X_2$ is O or $NR_5$, where $R_5$ is selected from the group consisting of hydrogen, and $C_1$–$C_6$ straight or branched alkyl or alkenyl;

$R_4$ is selected from the group consisting of phenyl, benzyl, $C_1$–$C_5$ straight or branched alkyl or alkenyl, and $C_1$–$C_5$ straight or branched alkyl or alkenyl substituted with phenyl; or a pharmaceutically acceptable salt or hydrate thereof.

2. The method of claim 1 wherein the compound is of the formula:

II

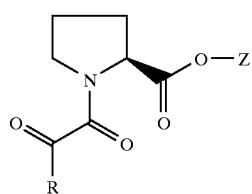

wherein

R is a $C_1$–$C_9$ straight or branched chain alkyl or alkenyl group optionally substituted with $C_3$–$C_8$ cycloalkyl, $C_5$–$C_7$ cycloalkenyl, or $Ar_1$, where said alkyl, alkenyl, cycloalkyl or cycloalkenyl groups are optionally substituted with $C_1$–$C_4$ alkyl, $C_1$–$C_4$ alkenyl, or hydroxy, and where $Ar_1$ is selected from the group consisting of 1-naphthyl, 2-naphthyl, 2-indolyl, 3-indolyl, 2-furyl, 3-furyl, 2-thiazolyl, 2-thienyl, 3-thienyl, 2-pyridyl, 3-pyridyl, 4-pyridyl, and phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino;

Z is a $C_2$–$C_6$ straight or branched chain alkyl or alkenyl, wherein the $C_2$–$C_6$ straight or branched chain alkyl is substituted in one or more positions with $Ar_1$ as defined above, $C_3$–$C_8$ cycloalkyl, or cycloalkyl connected by a $C_1$–$C_6$ straight alkyl or alkenyl chain; or a pharmaceutically acceptable salt or hydrate thereof.

3. The method of claim 1 wherein the compound is selected from the group consisting of:

3-phenyl-1-propyl (2S)-1-(3,3-dimethyl-1,2-dioxopentyl)-2-pyrrolidinecarboxylate, 3-phenyl-1-prop-2-(E)-enyl (2S)-1-(3,3,-dimethyl-1,2-dioxopentyl)-2-pyrrolidinecarboxylate, 3-(3,4,5-trimethoxyphenyl)-1-propyl (2S)-1-(3,3-dimethyl-1,2-dioxopentyl)-2-pyrrolidinecarboxylate, 3-(3,4,5-trimethoxyphenyl)-1-prop-2-(E)-enyl (2S)-1-(3,3-dimethyl-1,2-dioxopentyl)-2-pyrrolidinecarboxylate, 3-(4,5-methylenedioxyphenyl)-1-propyl(2S)-1-(3,3,dimethyl-1,2-dioxopentyl)-2-pyrrolidinecarboxylate, 3-(4,5-methylenedioxyphenyl)-1-prop-2-(E)-enyl (2S)-1-(3,3-dimethyl-1,2-dioxopentyl)-2-pyrrolidinecarboxylate, 3-cyclohexyl-1-propyl (2S)-1-(3,3-dimethyl-1,2-dioxopentyl)-2-pyrrolidinecarboxylate, 3-cyclohexyl-1-prop-2-(E)-enyl (2S)-1-(3,3-dimethyl-1,2-dioxopentyl)-2-pyrrolidinecarboxylate, (1R)-1,3-diphenyl-1-propyl (2S)-1-(3,3-dimethyl-1,2-dioxopentyl)-2-pyrrolidinecarboxylate, 3-phenyl-1-propyl (2S)-1-(1,2-dioxo-2-[2-furanyl])ethyl-2-pyrrolidinecarboxylate, 3-phenyl-1-propyl (2S)-1-(1,2-dioxo-2-[2-thienyl])entyl-2-pyrrolidinecarboxylate, 3-phenyl-1-propyl (2S)-1-(1,2-dioxo-2-[2-thiazolyl])ethyl-2-pyrrolidinecarboxylate, 3-phenyl-1-propyl (2S)-1-(1,2-dioxo-2,phenyl)ethyl-2-pyrrolidinecarboxylate, 3-(2,5-dimethoxyphenyl)-1-propyl (2S)-1-(3,3-dimethyl-1,2-dioxopentyl)-2-pyrrolidinecarboxylate, 3-(2,5-dimethoxyphenyl)-1-prop-2-(E)-enyl(2S)-1-(3,3-dimethyl-1,2-dioxopentyl)-2-pyrrolidinecarboxylate, 2-(3,4,5-trimethoxyphenyl)-1-ethyl (2S)-1-(3,3-dimethyl-1,2-dioxopentyl)-2-pyrrolidinecarboxylate, 3-(3-Pyridyl)-1-propyl(2S)-1-(3,3-dimethyl-1,2-dioxopentyl)-2-pyrrolidinecarboxylate, 3-(2-Pyridyl)-1-propyl(2S)-1-(3,3-dimethyl-1,2-dioxopentyl)-2-pyrrolidinecarboxylate, 3-(4-Pyridyl)-1-propyl(2S)-1-(3,3-dimethyl-1,2-dioxopentyl)-2-pyrrolidinecarboxylate, 3-phenyl-1-propyl (2S)-1-(2-cyclohexyl-1,2-dioxoethyl)-2-pyrrolidinecarboxylate, 3-phenyl-1-propyl (2S)-1-(2-tert-butyl-1,2-dioxoethyl)-2-pyrrolidinecarboxylate, 3-phenyl-1-propyl (2S)-1-(2-cyclohexylethyl-1,2-dioxoethyl)-2-pyrrolidinecarboxylate, 3-(3-Pyridyl)-1-propyl (2S)-1-(2-cyclohexylethyl-1,2-dioxoethyl)-2-pyrrolidinecarboxylate, 3-(3-Pyridyl)-1-propyl (2S)-1-(2-tert-butyl-1,2-dioxoethyl)-2-pyrrolidinecarboxylate, 3,3-diphenyl-1-propyl (2S)-1-(3,3-dimethyl-1,2-dioxopentyl)-2-pyrrolidinecarboxylate, 3-(3-Pyridyl)-1-propyl (2S)-1-(2-cyclohexyl-1,2-dioxoethyl)-2-pyrrolidinecarboxylate, 3-(3-Pyridyl)-1-propyl (2S)-N-([2-thienyl]glyoxyl) pyrrolidinecarboxylate, 3,3-Diphenyl-1-propyl (2S)-1-(3,3-dimethyl-1,2-dioxobutyl)-2-pyrrolidinecarboxylate, 3,3-Diphenyl-1-propyl (2S)-1-cyclohexylglyoxyl-2-pyrrolidinecarboxylate and 3,3-Diphenyl-1-propyl (2S)-1-(2-thienyl)glyoxyl-2-pyrrolidinecarboxylate, or a pharmaceutically acceptable salt, hydrate, or mixture thereof.

4. A method of preventing hair loss which comprises: administering to an animal in need thereof an effective amount of a compound of the formula:

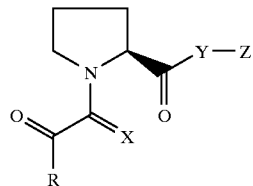
I wherein

R is selected from the group consisting of a $C_1$–$C_9$ straight or branched chain alkyl or alkenyl group optionally substituted with $C_3$–$C_8$ cycloalkyl, $C_5$–$C_7$ cycloalkenyl, and $Ar_1$, where said alkyl, alkenyl, cycloalkyl or cycloalkenyl groups are optionally substituted with $C_1$–$C_4$ alkyl, $C_1$–$C_4$ alkenyl, or hydroxy, where $Ar_1$ is selected from the group consisting of 1-naphthyl, 2-naphthyl, 2-indolyl, 3-indolyl, 2-furyl, 3-furyl, 2-thiazolyl, 2-thienyl, 3-thienyl, 2-pyridyl, 3-pyridyl, 4-pyridyl, and phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino;

X is selected from the group consisting of oxygen, sulphur, methylene, or $H_2$;

Y is selected from the group consisting of oxygen or $NR_2$, where $R_2$ is hydrogen or $C^1$–$C_6$ alkyl; and Z is selected from the group consisting of $C_2$–$C_6$ straight or branched chain alkyl or alkenyl, wherein the $C_2$–$C_6$ straight or branched chain alkyl is substituted in one or more positions with $Ar_1$ as defined above, $C_3$–$C_8$ cycloalkyl, or cycloalkyl connected by a $C_1$–$C_6$ straight alkyl or alkenyl chain; or Z is a fragment having the following formula:

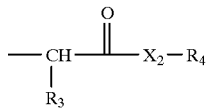

wherein $R_3$ is selected from the group consisting of $C_1$–$C_8$ straight or branched alkyl optionally substituted with $C_3$–$C_8$ cycloalkyl, $Ar_1$ as defined above, and unsubstituted $Ar_1$;

$X_2$ is O or $NR_5$, where $R_5$ is selected from the group consisting of hydrogen, and $C_1$–$C_6$ straight or branched alkyl or alkenyl;

$R_4$ is selected from the group consisting of phenyl, benzyl, $C_1$–$C_5$ straight or branched alkyl or alkenyl, and $C_1$–$C_5$ straight or branched alkyl or alkenyl substituted with phenyl; or a pharmaceutically acceptable salt or hydrate thereof.

5. The method of claim 4 wherein the compound is of the formula:

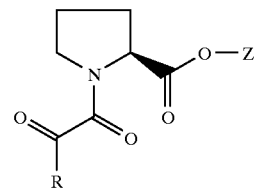
II wherein

R is a $C_1$–$C_9$ straight or branched chain alkyl or alkenyl group optionally substituted with $C_3$–$C_8$ cycloalkyl, $C_5$–$C_7$ cycloalkenyl, or $Ar_1$, where said alkyl, alkenyl, cycloalkyl or cycloalkenyl groups are optionally substituted with $C_1$–$C_4$ alkyl, $C_1$–$C_4$ alkenyl, or hydroxy, and where $Ar_1$ is selected from the group consisting of 1-naphthyl, 2-naphthyl, 2-indolyl, 3-indolyl, 2-furyl, 3-furyl, 2-thiazolyl, 2-thienyl, 3-thienyl, 2-pyridyl, 3-pyridyl, 4-pyridyl, and phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino;

Z is a $C_2$–$C_6$ straight or branched chain alkyl or alkenyl, wherein the $C_2$–$C_6$ straight or branched chain alkyl is substituted in one or more positions with $Ar_1$ as defined above, $C_3$–$C_8$ cycloalkyl, or cycloalkyl connected by a $C_1$–$C_6$ straight alkyl or alkenyl chain; or a pharmaceutically acceptable salt or hydrate thereof.

6. The method of claim 4 wherein the compound is selected from the group consisting of:

3-phenyl-1-propyl (2S)-1-(3,3-dimethyl-1,2-dioxopentyl)-2-pyrrolidinecarboxylate, 3-phenyl-1-prop-2-(E)-enyl (2S)-1-(3,3,-dimethyl-1,2-dioxopentyl)-2-pyrrolidinecarboxylate, 3-(3,4,5-trimethoxyphenyl)-1-propyl (2S)-1-(3,3-dimethyl-1,2-dioxopentyl)-2-pyrrolidinecarboxylate, 3-(3,4,5-trimethoxyphenyl)-1-prop-2-(E)-enyl (2S)-1-(3,3-dimethyl-1,2-dioxopentyl)-2-pyrrolidinecarboxylate, 3-(4,5-methylenedioxyphenyl)-1-propyl (2S)-1-(3,3,dimethyl-1,2-dioxopentyl)-2-pyrrolidinecarboxylate, 3-(4,5-methylenedioxyphenyl)-1-prop-2-(E)-enyl (2S)-1-(3,3-dimethyl-1,2-dioxopentyl)-2-pyrrolidinecarboxylate, 3-cyclohexyl-1-propyl(2S)-1-(3,3-dimethyl-1,2-dioxopentyl)-2-pyrrolidinecarboxylate, 3-cyclohexyl-1-prop-2-(E)-enyl (2S)-1-(3,3-dimethyl-1,2-dioxopentyl)-2-pyrrolidinecarboxylate, (1R)-1,3-diphenyl-1-propyl (2S)-1-(3,3-dimethyl-1,2-dioxopentyl)-2-pyrrolidinecarboxylate, 3-phenyl-1-propyl (2S)-1-(1,2-dioxo-2-[2-furanyl])ethyl-2-pyrrolidinecarboxylate, 3-phenyl-1-propyl (2S)-1-(1,2-dioxo-2-[2-thienyl])entyl-2-pyrrolidinecarboxylate, 3-phenyl-1-propyl (2S)-1-(1,2-dioxo-2-[2-thiazolyl])ethyl-2-pyrrolidinecarboxylate, 3-phenyl-1-propyl (2S)-1-(1,2-dioxo-2,phenyl)ethyl-2-pyrrolidinecarboxylate, 3-(2,5-dimethoxyphenyl)-1-propyl (2S)-1-(3,3-dimethyl-1,2-dioxopentyl)-2-pyrrolidinecarboxylate, 3-(2,5-dimethoxyphenyl)-1-prop-2-(E)-enyl(2S)-1-(3,3-dimethyl-1,2-dioxopentyl)-2-pyrrolidinecarboxylate, 2-(3,4,5-trimethoxyphenyl)-1-ethyl (2S)-1-(3,3-dimethyl-1,2-dioxopentyl)-2-pyrrolidinecarboxylate, 3-(3-Pyridyl)-1-propyl(2S)-1-(3,3-dimethyl-1,2-dioxopentyl)-2pyrrolidinecarboxylate, 3-(2-Pyridyl)-1-propyl(2S)-1-(3,3-dimethyl-1,2-dioxopentyl)-2-pyrrolidinecarboxylate,
3-(4-Pyridyl)-1-propyl(2S)-1-(3,3-dimethyl-1,2-dioxopentyl)-2-pyrrolidinecarboxylate,
3-phenyl-1-propyl (2S)-1-(2-cyclohexyl-1,2-dioxoethyl)-2-pyrrolidinecarboxylate,
3-phenyl-1-propyl (2S)-1-(2-tert-butyl-1,2-dioxoethyl)-2-pyrrolidinecarboxylate,
3-phenyl-1-propyl (2S)-1-(2-cyclohexylethyl-1,2-dioxoethyl)-2-pyrrolidinecarboxylate,
3-(3-Pyridyl)-1-propyl (2S)-1-(2-cyclohexylethyl-1,2-dioxoethyl)-2-pyrrolidinecarboxylate,
3-(3-Pyridyl)-1-propyl (2S)-1-(2-tert-butyl-1,2-dioxoethyl)-2-pyrrolidinecarboxylate,
3,3-diphenyl-1-propyl (2S)-1-(3,3-dimethyl-1,2-dioxopentyl)-2-pyrrolidinecarboxylate,
3-(3-Pyridyl)-1-propyl (2S)-1-(2-cyclohexyl-1,2-dioxoethyl)-2-pyrrolidinecarboxylate,
3-(3-Pyridyl)-1-propyl (2S)-N-([2-thienyl]glyoxyl) pyrrolidinecarboxylate,
3,3-Diphenyl-1-propyl (2S)-1-(3,3-dimethyl-1,2-dioxobutyl)-2-pyrrolidinecarboxylate,
3,3-Diphenyl-1-propyl (2S)-1-cyclohexylglyoxyl-2-pyrrolidinecarboxylate and
3,3-Diphenyl-1-propyl (2S)-1-(2-thienyl)glyoxyl-2-pyrrolidinecarboxylate, or a pharmaceutically acceptable salt, hydrate, or mixture thereof.

7. A method of treating alopecia which comprises: administering to an animal an effective amount of a compound of the formula:

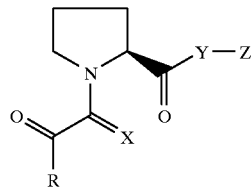

I wherein
R is selected from the group consisting of a $C_1$–$C_9$ straight or branched chain alkyl or alkenyl group optionally substituted with $C_3$–$C_8$ cycloalkyl, $C_5$–$C_7$ cycloalkenyl, and $Ar_1$, where said alkyl, alkenyl, cycloalkyl or cycloalkenyl groups are optionally substituted with $C_1$–$C_4$ alkyl, $C_1$–$C_4$ alkenyl, or hydroxy, where $Ar_1$ is selected from the group consisting of 1-naphthyl, 2-naphthyl, 2-indolyl, 3-indolyl, 2-furyl, 3-furyl, 2-thiazolyl, 2-thienyl, 3-thienyl, 2-pyridyl, 3-pyridyl, 4-pyridyl, and phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino;
X is selected from the group consisting of oxygen, sulphur, methylene, or $H_2$;
Y is selected from the group consisting of oxygen or $NR_2$, where $R_2$ is hydrogen or $C^1$–$C_6$ alkyl; and
Z is selected from the group consisting of $C_2$–$C_6$ straight or branched chain alkyl or alkenyl,
wherein the $C_2$–$C_6$ straight or branched chain alkyl is substituted in one or more positions with $Ar_1$ as defined above, $C_3$–$C_8$ cycloalkyl, or cycloalkyl connected by a $C_1$–$C_6$ straight alkyl or alkenyl chain; or Z is a fragment having the following formula:

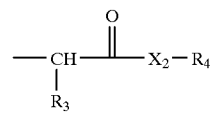

wherein
$R_3$ is selected from the group consisting of $C_1$–$C_8$ straight or branched alkyl optionally substituted with $C_3$–$C_8$ cycloalkyl, $Ar_1$ as defined above, and unsubstituted $Ar_1$;
$X_2$ is O or $NR_5$, where $R_5$ is selected from the group consisting of hydrogen, and $C_1$–$C_6$ straight or branched alkyl or alkenyl;
$R_4$ is selected from the group consisting of phenyl, benzyl, $C_1$–$C_5$ straight or branched alkyl or alkenyl, and $C_1$–$C_5$ straight or branched alkyl or alkenyl substituted with phenyl; or a pharmaceutically acceptable salt or hydrate thereof.

8. The method of claim 7 wherein the compound is of the formula:

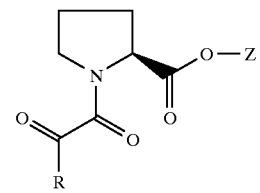

II wherein
R is a $C_1$–$C_9$ straight or branched chain alkyl or alkenyl group optionally substituted with $C_3$–$C_8$ cycloalkyl, $C_5$–$C_7$ cycloalkenyl, or $Ar_1$, where said alkyl, alkenyl, cycloalkyl or cycloalkenyl groups are optionally substituted with $C_1$–$C_4$ alkyl, $C_1$–$C_4$ alkenyl, or hydroxy, and where $Ar_1$ is selected from the group consisting of 1-naphthyl, 2-naphthyl, 2-indolyl, 3-indolyl, 2-furyl, 3-furyl, 2-thiazolyl, 2-thienyl, 3-thienyl, 2-pyridyl, 3-pyridyl, 4-pyridyl, and phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino;
Z is a $C_2$–$C_6$ straight or branched chain alkyl or alkenyl, wherein the $C_2$–$C_6$ straight or branched chain alkyl is substituted in one or more positions with $Ar_1$ as defined above, $C_3$–$C_8$ cycloalkyl, or cycloalkyl connected by a $C_1$–$C_6$ straight alkyl or alkenyl chain; or a pharmaceutically acceptable salt or hydrate thereof.

9. The method of claim 7 wherein the compound is selected from the group consisting of:
3-phenyl-1-propyl (2S)-1-(3,3-dimethyl-1,2-dioxopentyl)-2-pyrrolidinecarboxylate,
3-phenyl-1-prop-2-(E)-enyl (2S)-1-(3,3,-dimethyl-1,2-dioxopentyl)-2-pyrrolidinecarboxylate,
3-(3,4,5-trimethoxyphenyl)-1-propyl (2S)-1-(3,3-dimethyl-1,2-dioxopentyl)-2-pyrrolidinecarboxylate,
3-(3,4,5-trimethoxyphenyl)-1-prop-2-(E)-enyl (2S)-1-(3,3-dimethyl-1,2-dioxopentyl)-2-pyrrolidinecarboxylate,
3-(4,5-methylenedioxyphenyl)-1-propyl(2S)-1-(3,3,dimethyl-1,2dioxopentyl)-2-pyrrolidinecarboxylate, 3-(4,5-methylenedioxyphenyl)-1-prop-2-(E)-enyl (2S)-1-(3, 3-dimethyl-1,2-dioxopentyl)-2-pyrrolidinecarboxylate,
3-cyclohexyl-1-propyl (2S)-1-(3,3-dimethyl-1,2-dioxopentyl)-2-pyrrolidinecarboxylate,
3-cyclohexyl-1-prop-2-(E)-enyl (2S)-1-(3,3-dimethyl-1,2-dioxopentyl)-2-pyrrolidinecarboxylate,
(1R)-1,3-diphenyl-1-propyl (2S)-1-(3,3-dimethyl-1,2-dioxopentyl)-2-pyrrolidinecarboxylate,
3-phenyl-1-propyl (2S)-1-(1,2-dioxo-2-[2-furanyl])ethyl-2-pyrrolidinecarboxylate,
3-phenyl-1-propyl (2S)-1-(1,2-dioxo-2-[2-thienyl])entyl-2-pyrrolidinecarboxylate,
3-phenyl-1-propyl (2S)-1-(1,2-dioxo-2-[2-thiazolyl])ethyl-2-pyrrolidinecarboxylate,
3-phenyl-1-propyl (2S)-1-(1,2-dioxo-2,phenyl)ethyl-2-pyrrolidinecarboxylate,
3-(2,5-dimethoxyphenyl)-1-propyl (2S)-1-(3,3-dimethyl-1, 2-dioxopentyl)-2-pyrrolidinecarboxylate,
3-(2,5-dimethoxyphenyl)-1-prop-2-(E)-enyl(2S)-1-(3,3-dimethyl-1,2-dioxopentyl)-2-pyrrolidinecarboxylate,
2-(3,4,5-trimethoxyphenyl)-1-ethyl (2S)-1-(3,3-dimethyl-1, 2-dioxopentyl)-2-pyrrolidinecarboxylate,
3-(3-Pyridyl)-1-propyl(2S)-1-(3,3-dimethyl-1,2-dioxopentyl)-2-pyrrolidinecarboxylate,
3-(2-Pyridyl)-1-propyl(2S)-1-(3,3-dimethyl-1,2-dioxopentyl)-2-pyrrolidinecarboxylate,
3-(4-Pyridyl)-1-propyl(2S)-1-(3,3-dimethyl-1,2-dioxopentyl)-2-pyrrolidinecarboxylate,
3-phenyl-1-propyl (2S)-1-(2-cyclohexyl-1,2-dioxoethyl)-2-pyrrolidinecarboxylate,
3-phenyl-1-propyl (2S)-1-(2-tert-butyl-1,2-dioxoethyl)-2-pyrrolidinecarboxylate,
3-phenyl-1-propyl (2S)-1-(2-cyclohexylethyl-1,2-dioxoethyl)-2-pyrrolidinecarboxylate,
3-(3-Pyridyl)-1-propyl (2S)-1-(2-cyclohexylethyl-1,2-dioxoethyl)-2-pyrrolidinecarboxylate,
3-(3-Pyridyl)-1-propyl (2S)-1-(2-tert-butyl-1,2-dioxoethyl)-2-pyrrolidinecarboxylate,
3,3-diphenyl-1-propyl (2S)-1-(3,3-dimethyl-1,2-dioxopentyl)-2-pyrrolidinecarboxylate,
3-(3-Pyridyl)-1-propyl (2S)-1-(2-cyclohexyl-1,2-dioxoethyl)-2-pyrrolidinecarboxylate,
3-(3-Pyridyl)-1-propyl (2S)-N-([2-thienyl]glyoxyl) pyrrolidinecarboxylate,
3,3-Diphenyl-1-propyl (2S)-1-(3,3-dimethyl-1,2-dioxobutyl)-2-pyrrolidinecarboxylate,
3,3-Diphenyl-1-propyl (2S)-1-cyclohexylglyoxyl-2-pyrrolidinecarboxylate and
3,3-Diphenyl-1-propyl (2S)-1-(2-thienyl)glyoxyl-2-pyrrolidinecarboxylate, or a pharmaceutically acceptable salt, hydrate, or mixture thereof.

10. A method of treating hair loss which comprises: administering to an animal an effective amount of a compound of the formula:

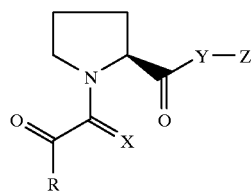

I wherein
R is selected from the group consisting of a $C_1$–$C_9$ straight or branched chain alkyl or alkenyl group optionally substituted with $C_3$–$C_8$ cycloalkyl, $C_5$–$C_7$ cycloalkenyl, and $Ar_1$, where said alkyl, alkenyl, cycloalkyl or cycloalkenyl groups are optionally substituted with $C_1$–$C_4$ alkyl, $C_1$–$C_4$ alkenyl, or hydroxy, where $Ar_1$ is selected from the group consisting of 1-naphthyl, 2-naphthyl, 2-indolyl, 3-indolyl, 2-furyl, 3-furyl, 2-thiazolyl, 2-thienyl, 3-thienyl, 2-pyridyl, 3-pyridyl, 4-pyridyl, and phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and;

X is selected from the group consisting of oxygen, sulphur, methylene, or $H_2$;

Y is selected from the group consisting of oxygen or $NR_2$, where $R_2$ is hydrogen or $C^1$–$C_6$ alkyl; and Z is selected from the group consisting Of $C_2$–$C_6$ straight or branched chain alkyl or alkenyl, wherein the $C_2$–$C_6$ straight or branched chain alkyl is substituted in one or more positions with $Ar_1$ as defined above, $C_3$–$C_8$ cycloalkyl, or cycloalkyl connected by a $C_1$–$C_6$ straight alkyl or alkenyl chain; or Z is a fragment having the following formula:

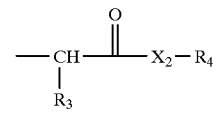

wherein
$R_3$ is selected from the group consisting of $C_1$–$C_8$ straight or branched alkyl optionally substituted with $C_3$–$C_8$ cycloalkyl, $Ar_1$ as defined above, and unsubstituted $Ar_1$;

$X_2$ is O or $NR_5$, where $R_5$ is selected from the group consisting of hydrogen, and $C_1$–$C_6$ straight or branched alkyl or alkenyl;

$R_4$ is selected from the group consisting of phenyl, benzyl, $C_1$–$C_5$ straight or branched alkyl or alkenyl, and $C_1$–$C_5$ straight or branched alkyl or alkenyl substituted with phenyl; or a pharmaceutically acceptable salt or hydrate thereof.

11. The method of claim 10 wherein the compound is of the formula:

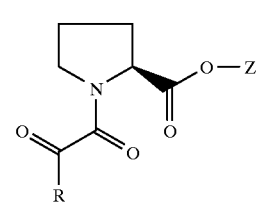

II wherein
R is a $C_1$–$C_9$ straight or branched chain alkyl or alkenyl group optionally substituted with $C_3$–$C_8$ cycloalkyl, $C_5$–$C_7$ cycloalkenyl, or $Ar_1$, where said alkyl, alkenyl, cycloalkyl or cycloalkenyl groups are optionally substituted with $C_1$–$C_4$ alkyl, $C_1$–$C_4$ alkenyl, or hydroxy, and where $Ar_1$ is selected from the group consisting of 1-naphthyl, 2-naphthyl, 2-indolyl, 3-indolyl, 2-furyl, 3-furyl, 2-thiazolyl, 2-thienyl, 3-thienyl, 2-pyridyl, 3-pyridyl, 4-pyridyl, and phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino;

Z is a $C_2$–$C_6$ straight or branched chain alkyl or alkenyl, wherein the $C_2$–$C_6$ straight or branched chain alkyl is substituted in one or more positions with $Ar_1$ as defined above, $C_3$–$C_8$ cycloalkyl, or cycloalkyl connected by a $C_1$–$C_6$ straight alkyl or alkenyl chain; or a pharmaceutically acceptable salt or hydrate thereof.

12. The method of claim 10 wherein the compound is selected from the group consisting of:
3-phenyl-1-propyl (2S)-1-(3,3-dimethyl-1,2-dioxopentyl)-2-pyrrolidinecarboxylate,
3-phenyl-1-prop-2-(E)-enyl (2S)-1-(3,3,-dimethyl-1,2-dioxopentyl)-2-pyrrolidinecarboxylate,
3-(3,4,5-trimethoxyphenyl)-1-propyl (2S)-1-(3,3-dimethyl-1,2-dioxopentyl)-2-pyrrolidinecarboxylate,
3-(3,4,5-trimethoxyphenyl)-1-prop-2-(E)-enyl (2S)-1-(3,3-dimethyl-1,2-dioxopentyl)-2-pyrrolidinecarboxlate
3-(4,5-methylenedioxyphenyl)-1-propyl(2S)-1-(3,3,dimethyl-1,2-dioxopentyl)-2-pyrrolidinecarboxylate,
3-(4,5-methylenedioxyphenyl)-1-prop-2-(E)-enyl (2S)-1-(3,3-dimethyl-1,2-dioxopentyl)-2-pyrrolidinecarboxylate,
3-cyclohexyl-1-propyl (2S)-1-(3,3-dimethyl-1,2-dioxopentyl)-2-pyrrolidinecarboxylate,
3-cyclohexyl-1-prop-2-(E)-enyl (2S)-1-(3,3-dimethyl-1,2-dioxopentyl)-2-pyrrolidinecarboxylate,
(1R)-1,3-diphenyl-1-propyl (2S)-1-(3,3-dimethyl-1,2-dioxopentyl)-2-pyrrolidinecarboxylate,
3-phenyl-1-propyl (2S)-1-(1,2-dioxo-2-[2-furanyl])ethyl-2-pyrrolidinecarboxylate,
3-phenyl-1-propyl (2S)-1-(1,2-dioxo-2-[2-thienyl])entyl-2-pyrrolidinecarboxylate,
3-phenyl-1-propyl (2S)-1-(1,2-dioxo-2-[2-thiazolyl])ethyl-2-pyrrolidinecarboxylate,
3-phenyl-1-propyl (2S)-1-(1,2-dioxo-2,phenyl)ethyl-2-pyrrolidinecarboxylate,
3-(2,5-dimethoxyphenyl)-1-propyl (2S)-1-(3,3-dimethyl-1,2-dioxopentyl)-2-pyrrolidinecarboxylate,
3-(2,5-dimethoxyphenyl)-1-prop-2-(E)-enyl(2S)-1-(3,3-dimethyl1,2-dioxopentyl)-2-pyrrolidinecarboxylate,
2-(3,4,5-trimethoxyphenyl)-1-ethyl (2S)-1-(3,3-dimethyl-1,2-dioxopentyl)-2-pyrrolidinecarboxylate,
3-(3-Pyridyl)-1-propyl(2S)-1-(3,3-dimethyl-1,2-dioxopentyl)-2-pyrrolidinecarboxylate,
3-(2-Pyridyl)-1-propyl(2S)-1-(3,3-dimethyl-1,2-dioxopentyl)-2-pyrrolidinecarboxylate,
3-(4-Pyridyl)-1-propyl(2S)-1-(3,3-dimethyl-1,2-dioxopentyl)-2-pyrrolidinecarboxylate,
3-phenyl-1-propyl (2S)-1-(2-cyclohexyl-1,2-dioxopentyl)-2-pyrrolidinecarboxylate,
3-phenyl-1-propyl (2S)-1-(2-tert-butyl-1,2-dioxopentyl)-2-pyrrolidinecarboxylate,
3-phenyl-1-propyl (2S)-1-(2-cyclohexylethyl-1,2-dioxopentyl)-2-pyrrolidinecarboxylate,
3-(3-Pyridyl)-1-propyl (2S)-1-(2-cyclohexylethyl-1,2-dioxopentyl)-2-pyrrolidinecarboxylate,
3-(3-Pyridyl)-1-propyl (2S)-1-(2-tert-butyl-1,2-dioxopentyl)-2-pyrrolidinecarboxylate,
3,3-diphenyl-1-propyl (2S)-1-(3,3-dimethyl-1,2-dioxopentyl)-2-pyrrolidinecarboxylate,
3-(3-Pyridyl)-1-propyl (2S)-1-(2-cyclohexyl-1,2-dioxopentyl)-2-pyrrolidinecarboxylate,
3-(3-Pyridyl)-1-propyl (2S)-N-([2-thienyl]glyoxyl) pyrrolidinecarboxylate,
3,3-Diphenyl-1-propyl (2S)-1-(3,3-dimethyl-1,2-dioxobutyl)-2-pyrrolidinecarboxylate,
3,3-Diphenyl-1-propyl (2S)-1-cyclohexylglyoxyl-2-pyrrolidinecarboxylate, and
3,3-Diphenyl-1-propyl(2S)-1-(2-thienyl)glyoxyl-2-pyrrolidinecarboxylate, or a pharmaceutically acceptable salt, hydrate, or mixture thereof.

13. A method of treating hair loss associated with cancer therapy, wherein the cancer therapy is selected from the group consisting of radiation and chemotherapy, which comprises: administering to an animal an effective amount of a compound of the formula:

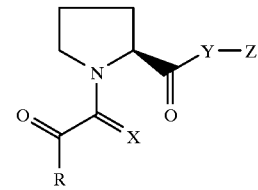

I wherein
R is selected from the group consisting of a $C_1$–$C_9$ straight or branched chain alkyl or alkenyl group optionally substituted with $C_3$–$C_8$ cycloalkyl, $C_5$–$C_7$ cycloalkenyl, and $Ar_1$, where said alkyl, alkenyl, cycloalkyl or cycloalkenyl groups are optionally substituted with $C_1$–$C_4$ alkyl, $C_1$–$C_4$ alkenyl, or hydroxy, where $Ar_1$ is selected from the group consisting of 1-naphthyl, 2-naphthyl, 2-indolyl, 3-indolyl, 2-furyl, 3-furyl, 2-thiazolyl, 2-thienyl, 3-thienyl, 2-pyridyl, 3-pyridyl, 4-pyridyl, and phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino;

X is selected from the group consisting of oxygen, sulphur, methylene, or $H_2$;

Y is selected from the group consisting of oxygen or $NR_2$, where $R_2$ is hydrogen or $C_1$–$C_6$ alkyl; and Z is selected from the group consisting of $C_2$–$C_6$ straight or branched chain alkyl or alkenyl, wherein the $C_2$–$C_6$ straight or branched chain alkyl is substituted in one or more positions with $Ar_1$ as defined above, $C_3$–$C_8$ cycloalkyl, or cycloalkyl connected by a $C_1$–$C_6$ straight alkyl or alkenyl chain; or Z is a fragment having the following formula:

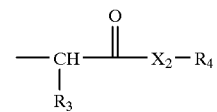

wherein
$R_3$ is selected from the group consisting of $C_1$–$C_8$ straight or branched alkyl optionally substituted with $C_3$–$C_8$ cycloalkyl, $Ar_1$ as defined above, and unsubstituted $Ar_1$;
$X_2$ is O or $NR_5$, where $R_5$ is selected from the group consisting of hydrogen, and $C_1$–$C_6$ straight or branched alkyl or alkenyl;
$R_4$ is selected from the group consisting of phenyl, benzyl, $C_1$–$C_5$ straight or branched alkyl or alkenyl, and C₁–C₅ straight or branched alkyl or alkenyl substituted with phenyl; or a pharmaceutically acceptable salt or hydrate thereof.

14. The method of claim 13 wherein the compound is of the formula:

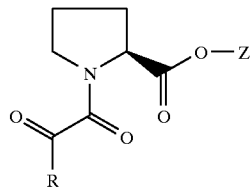

II wherein
R is a $C_1$–$C_9$ straight or branched chain alkyl or alkenyl group optionally substituted with $C_3$–$C_8$ cycloalkyl, $C_5$–$C_7$ cycloalkenyl, or $Ar_1$, where said alkyl, alkenyl, cycloalkyl or cycloalkenyl groups are optionally substituted with $C_1$–$C_4$ alkyl, $C_1$–$C_4$ alkenyl, or hydroxy, and where $Ar_1$ is selected from the group consisting of 1-naphthyl, 2-naphthyl, 2-indolyl, 3-indolyl, 2-furyl, 3-furyl, 2-thiazolyl, 2-thienyl, 3-thienyl, 2-pyridyl, 3-pyridyl, 4-pyridyl, and phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino;

Z is a $C_2$–$C_6$ straight or branched chain alkyl or alkenyl, wherein the $C_2$–$C_6$ straight or branched chain alkyl is substituted in one or more positions with $Ar_1$ as defined above, $C_3$–$C_8$ cycloalkyl, or cycloalkyl connected by a $C_1$–$C_6$ straight alkyl or alkenyl chain; or a pharmaceutically acceptable salt or hydrate thereof.

15. The method of claim 13 wherein the compound is selected from the group consisting of:
3-phenyl-1-propyl (2S)-1-(3,3-dimethyl-1,2-dioxopentyl)-2-pyrrolidinecarboxylate,
3-phenyl-1-prop-2-(E)-enyl (2S)-1-(3,3,-dimethyl-1,2-dioxopentyl)-2-pyrrolidinecarboxylate,
3-(3,4,5-trimethoxyphenyl)-1-propyl (2S)-1-(3,3-dimethyl-1,2-dioxopentyl)-2-pyrrolidinecarboxylate,
3-(3,4,5-trimethoxyphenyl)-1-prop-2-(E)-enyl (2S)-1-(3,3-dimethyl-1,2-dioxopentyl)-2-pyrrolidinecarboxylate,
3-(4,5-methylenedioxyphenyl)-1-propyl(2S)-1-(3,3,-dimethyl-1,2dioxopentyl)-2-pyrrolidinecarboxylate,
3-(4,5-methylenedioxyphenyl)-1-prop-2-(E)-enyl (2S)-1-(3,3-dimethyl-1,2-dioxopentyl)-2-pyrrolidinecarboxylate,
3-cyclohexyl-1-propyl (2S)-1-(3,3-dimethyl-1,2-dioxopentyl)-2-pyrrolidinecarboxylate,
3-cyclohexyl-1-prop-2-(E)-enyl (2S)-1-(3,3-dimethyl-1,2dioxopentyl)-2-pyrrolidinecarboxylate,
(1R)-1,3-diphenyl-1-propyl (2S)-1-(3,3-dimethyl-1,2-dioxopentyl)-2-pyrrolidinecarboxylate,
3-phenyl-1-propyl (2S)-1-(1,2-dioxo-2-[2-furanyl])ethyl-2-pyrrolidinecarboxylate,
3-phenyl-1-propyl (2S)-1-(1,2-dioxo-2-[2-thienyl])entyl-2-pyrrolidinecarboxylate,
3-phenyl-1-propyl (2S)-1-(1,2-dioxo-2-[2-thiazolyl])ethyl-2-pyrrolidinecarboxylate,
3-phenyl-1-propyl (2S)-1-(1,2-dioxo-2,phenyl)ethyl-2-pyrrolidinecarboxylate,
3-(2,5-dimethoxyphenyl)-1-propyl (2S)-1-(3,3-dimethyl-1,2-dioxopentyl)-2-pyrrolidinecarboxylate,
3-(2,5-dimethoxyphenyl)-1-prop-2-(E)-enyl(2S)-1-(3,3-dimethyl-1,2-dioxopentyl)-2-pyrrolidinecarboxylate,
2-(3,4,5-trimethoxyphenyl)-1-ethyl (2S)-1-(3,3-dimethyl-1,2-dioxopentyl)-2-pyrrolidinecarboxylate,
3-(3-Pyridyl)-1-propyl(2S)-1-(3,3-dimethyl-1,2-dioxopentyl)-2-pyrrolidinecarboxylate,
3-(2-Pyridyl)-1-propyl(2S)-1-(3,3-dimethyl-1,2-dioxopentyl)-2-pyrrolidinecarboxylate,
3-(4-Pyridyl)-1-propyl(2S)-1-(3,3-dimethyl-1,2-dioxopentyl)-2pyrrolidinecarboxylate,
3-phenyl-1-propyl (2S)-1-(2-cyclohexyl-1,2-dioxopentyl)-2-pyrrolidinecarboxylate,
3-phenyl-1-propyl (2S)-1-(2-tert-butyl-1,2-dioxopentyl)-2-pyrrolidinecarboxylate,
3-phenyl-1-propyl (2S)-1-(2-cyclohexylethyl-1,2-dioxopentyl)-2-pyrrolidinecarboxylate,
3-(3-Pyridyl)-1-propyl (2S)-1-(2-cyclohexylethyl-1,2-dioxopentyl)-2-pyrrolidinecarboxylate,
3-(3-Pyridyl)-1-propyl (2S)-1-(2-tert-butyl-1,2-dioxopentyl)-2-pyrrolidinecarboxylate,
3,3-diphenyl-1-propyl (2S)-1-(3,3-dimethyl-1,2-dioxopentyl)-2-pyrrolidinecarboxylate,
3-(3-Pyridyl)-1-propyl (2S)-1-(2-cyclohexyl-1,2-dioxopentyl)-2-pyrrolidinecarboxylate,
3-(3-Pyridyl)-1-propyl (2S)-N-([2-thienyl]glyoxyl) pyrrolidinecarboxylate,
3,3-Diphenyl-1-propyl (2S)-1-(3,3-dimethyl-1,2-dioxobutyl)-2-pyrrolidinecarboxylate,
3,3-Diphenyl-1-propyl (2S)-1-cyclohexylglyoxyl-2-pyrrolidinecarboxylate and
3,3-Diphenyl-1-propyl(2S)-1-(2-thienyl)glyoxyl-2-pyrrolidinecarboxylate, or a pharmaceutically acceptable salt, hydrate, or mixture thereof.

* * * * *

UNITED STATES PATENT AND TRADEMARK OFFICE
CERTIFICATE OF CORRECTION

PATENT NO. : 5,945,441
DATED : August 31, 1999
INVENTOR(S) : Joseph P. STEINER et al.

It is certified that error appears in the above-identified patent and that said Letters Patent is hereby corrected as shown below:

On the cover page, in Assignee Section [73], please replace "Gpi Nil Holdings, Inc." with
--GPI NIL Holdings, Inc.--.

Signed and Sealed this

Twenty-first Day of March, 2000

*Attest:*

Q. TODD DICKINSON

*Attesting Officer*   Commissioner of Patents and Trademarks

UNITED STATES PATENT AND TRADEMARK OFFICE
CERTIFICATE OF CORRECTION

PATENT NO. : 5,945,441
DATED : August 31, 1999
INVENTOR(S) : Joseph P. STEINER et al.

It is certified that error appears in the above-identified patent and that said Letters Patent is hereby corrected as shown below:

Column 16, line 67, please replace "dioxopentyl-2pyrrolidin
  ecarboxylate" with --dioxopentyl-2-pyrrolidinecarboxylate--.

Column 18, line 67, please replace
  "dimethyl-1,2dioxopentyl)-2-pyrrolidinecarboxylate"
with
  --dimethyl-1,2-dioxopentyl)-2-pyrrolidinecarboxylate--.

Column 20, line 13, after "benzyloxy, and" and before
  ";", please insert --amino--.

Column 20, line 18, after "group consisting" and before
  "$C_2$-$C_6$ straight", please replace "Of" with --of--.

Column 21, line 43, please replace
  "dimethyl1,2-dioxopentyl)-2-pyrrolidinecarboxylate"
with
  --dimethyl-1,2-dioxopentyl)-2-pyrrolidinecarboxylate--.

Column 21, line 52, please replace
  "(2S)-1-(2-cyclohexyl-1,2-dioxopentyl)-"
with
  --(2S)-1-(2-cyclohexyl-1,2-dioxoethyl)- --.

Column 21, line 54, please replace
  "(2S)-1-(2-tert-butyl-1,2-dioxopentyl)-2-"
with
  --(2S)-1-(2-tert-butyl-1,2-dioxoethyl)-2- --.

UNITED STATES PATENT AND TRADEMARK OFFICE
CERTIFICATE OF CORRECTION

PATENT NO. : 5,945,441
DATED : August 31, 1999
INVENTOR(S) : Joseph P. STEINER et al.

It is certified that error appears in the above-identified patent and that said Letters Patent is hereby corrected as shown below:

Column 21, line 57, please replace
  "dioxopentyl)-2-pyrrolidinecarboxylate"
with
  --dioxoethyl)-2-pyrrolidinecarboxylate--.

Column 21, line 59, please replace
  "dioxopentyl)-2-pyrrolidinecarboxylate"
with
  --dioxoethyl)-2-pyrrolidinecarboxylate--.

Column 21, line 61, please replace
  "dioxopentyl)-2-pyrrolidinecarboxylate"
with
  --dioxoethyl)-2-pyrrolidinecarboxylate--.

Column 21, line 65, please replace
  "dioxopentyl)-2-pyrrolidinecarboxylate"
with
  --dioxoethyl)-2-pyrrolidinecarboxylate--.

Column 22, line 43, after "is hydrogen or" and before
  "alkyl; and", please replace "$C_1-C_6$" with --$C^1-C_6$--.

Column 23, line 48, please replace
  "dimethyl-1,2dioxopentyl)-2-pyrrolidinecarboxylate"
with
  --dimethyl-1,2-dioxopentyl)-2-pyrrolidinecarboxylate--

UNITED STATES PATENT AND TRADEMARK OFFICE
CERTIFICATE OF CORRECTION

PATENT NO. : 5,945,441                          Page 4 of 4
DATED      : August 31, 1999
INVENTOR(S): Joseph P. STEINER et al.

It is certified that error appears in the above-indentified patent and that said Letters Patent is hereby corrected as shown below:

Column 24, line 2, please replace
   "2dioxopentyl)-2-pyrrolidinecarboxylate"
with
   --2-dioxopentyl)-2-pyrrolidinecarboxylate--.

Column 24, line26, please replace
   "(2S)-1-(2-cyclohexyl-1,2-dioxopentyl)-
with
   --(2S)-1-(2-cyclohexyl-1,2-dioxoethyl)- --.

Column 24, line 28, please replace
   "(2S)-1-(2-tert-butyl-1,2-dioxopentyl)-2-"
with
   --(2S)-1-(2-tert-butyl-1,2-dioxoethyl)-2- --.

Column 24, line 31, please replace
   "dioxopentyl)-2-pyrrolidinecarboxylate"
with
   --dioxoethyl)-2-pyrrolidinecarboxylate--.

Column 24, line 34, please replace
   "dioxopentyl)-2-pyrrolidinecarboxylate"
with
   --dioxoethyl)-2-pyrrolidinecarboxylate--.

Column 24, line 36, please replace
   "dioxopentyl)-2-pyrrolidinecarboxylate"
with
   --dioxoethyl)-2-pyrrolidinecarboxylate--.

Column 24, line 40, please replace
   "dioxopentyl)-2-pyrrolidinecarboxylate"
with
   --dioxoethyl)-2-pyrrolidine carboxylate--.